United States Patent
Kamiguchi

(10) Patent No.: US 10,418,141 B2
(45) Date of Patent: Sep. 17, 2019

(54) CHARGED PARTICLE BEAM TREATMENT APPARATUS

(71) Applicant: SUMITOMO HEAVY INDUSTRIES, LTD., Tokyo (JP)

(72) Inventor: Nagaaki Kamiguchi, Kanagawa (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 74 days.

(21) Appl. No.: 15/655,645

(22) Filed: Jul. 20, 2017

(65) Prior Publication Data

US 2019/0027264 A1  Jan. 24, 2019

(51) Int. Cl.
*G21K 1/04* (2006.01)
*A61N 5/10* (2006.01)

(52) U.S. Cl.
CPC ......... *G21K 1/046* (2013.01); *A61N 5/1043* (2013.01); *A61N 5/1045* (2013.01); *A61N 5/1077* (2013.01); *A61N 2005/1087* (2013.01); *A61N 2005/1095* (2013.01)

(58) Field of Classification Search
CPC .. A61N 5/1045; A61N 5/1042; A61N 5/1077; A61N 5/10; A61N 2005/1087; A61N 2005/1095; G21K 1/046
See application file for complete search history.

(56) References Cited

U.S. PATENT DOCUMENTS

| | | | |
|---|---|---|---|
| 2006/0072849 A1* | 4/2006 | Marc | A61N 5/1042 382/291 |
| 2010/0034357 A1* | 2/2010 | Svesson | A61N 5/1042 378/152 |
| 2010/0252754 A1* | 10/2010 | Brown | A61N 5/1042 250/492.1 |
| 2012/0119105 A1* | 5/2012 | Iwata | G21K 1/10 250/396 ML |
| 2012/0264998 A1* | 10/2012 | Fujitaka | A61N 5/1036 600/1 |
| 2014/0235919 A1* | 8/2014 | Iwata | A61N 5/103 600/1 |

(Continued)

FOREIGN PATENT DOCUMENTS

| JP | 2010-029594 A | 2/2010 |
|---|---|---|
| JP | 2014-176546 A | 9/2014 |

*Primary Examiner* — Wyatt A Stoffa
(74) *Attorney, Agent, or Firm* — Michael Best & Friedrich LLP

(57) ABSTRACT

A charged particle beam treatment apparatus includes an accelerator that generates and emits a charged particle beam, an irradiation nozzle that irradiates an irradiation target body with the charged particle beam, and a transport line that connects the accelerator and the irradiation nozzle to each other so as to transport the charged particle beam. The irradiation nozzle has a scanning unit which can scan the irradiation target body with the charged particle beam within a predetermined maximum scanning range in a direction along the first axis and a direction along the second axis, and a multi-leaf collimator disposed on a downstream side from the scanning unit, and which regulates a shape of an irradiation field when the irradiation target body is irradiated with the charged particle beam. The multi-leaf collimator has a pair of leaf groups disposed to face each other across the reference axis.

3 Claims, 6 Drawing Sheets

(56) References Cited

U.S. PATENT DOCUMENTS

| | | | |
|---|---|---|---|
| 2015/0031933 A1* | 1/2015 | Yamamoto | A61N 5/1043 600/1 |
| 2015/0087887 A1* | 3/2015 | Iwata | A61N 5/103 600/1 |
| 2019/0001153 A1* | 1/2019 | Jones | A61N 5/1047 |
| 2019/0030372 A1* | 1/2019 | MacDonald | A61N 5/103 |

* cited by examiner

CHARGED PARTICLE BEAM TREATMENT APPARATUS

BACKGROUND

Technical Field

A certain embodiment of the present invention relates to a charged particle beam treatment apparatus.

Description of Related Art

In a charged particle beam treatment apparatus which performs treatment by irradiating an irradiation target body with a charged particle beam, a configuration including a multi-leaf collimator in an irradiation nozzle for irradiating the irradiation target body with the charged particle beam is known in the related art. The multi-leaf collimator includes a pair of leaf groups including a plurality of leaves, and moves the leaves, thereby causing an opening shape between the pair of leaf groups to correspond to an irradiation field of the charged particle beam.

SUMMARY

According to an embodiment of the present invention, there is provided a charged particle beam treatment apparatus which irradiates an irradiation target body with a charged particle beam. The charged particle beam treatment apparatus includes an accelerator that generates and emits the charged particle beam, an irradiation nozzle that irradiates the irradiation target body with the charged particle beam, and a transport line that connects the accelerator and the irradiation nozzle to each other so as to transport the charged particle beam. An axis orthogonal to a reference axis when the irradiation target body is irradiated with the charged particle beam is set to as a first axis, and an axis orthogonal to the reference axis and the first axis is set to as a second axis. The irradiation nozzle has a scanning unit which can scan the irradiation target body with the charged particle beam within a predetermined maximum scanning range in a direction along the first axis and a direction along the second axis, and a multi-leaf collimator which is disposed on a downstream side from the scanning unit, and which regulates a shape of an irradiation field when the irradiation target body is irradiated with the charged particle beam. The multi-leaf collimator has a pair of leaf groups disposed to face each other across the reference axis. The leaf group has a plurality of leaves which are arrayed in the direction along the first axis, which are independently movable forward and rearward in the direction along the second axis, and which blocks the charged particle beam, and a leaf drive unit which causes the leaves to move forward and rearward in the direction along the second axis. In at least a portion of the plurality of leaves, a length in the direction along the second axis is shorter than a half of a length along the second axis of the maximum scanning range.

DETAILED DESCRIPTION

Figure 1:
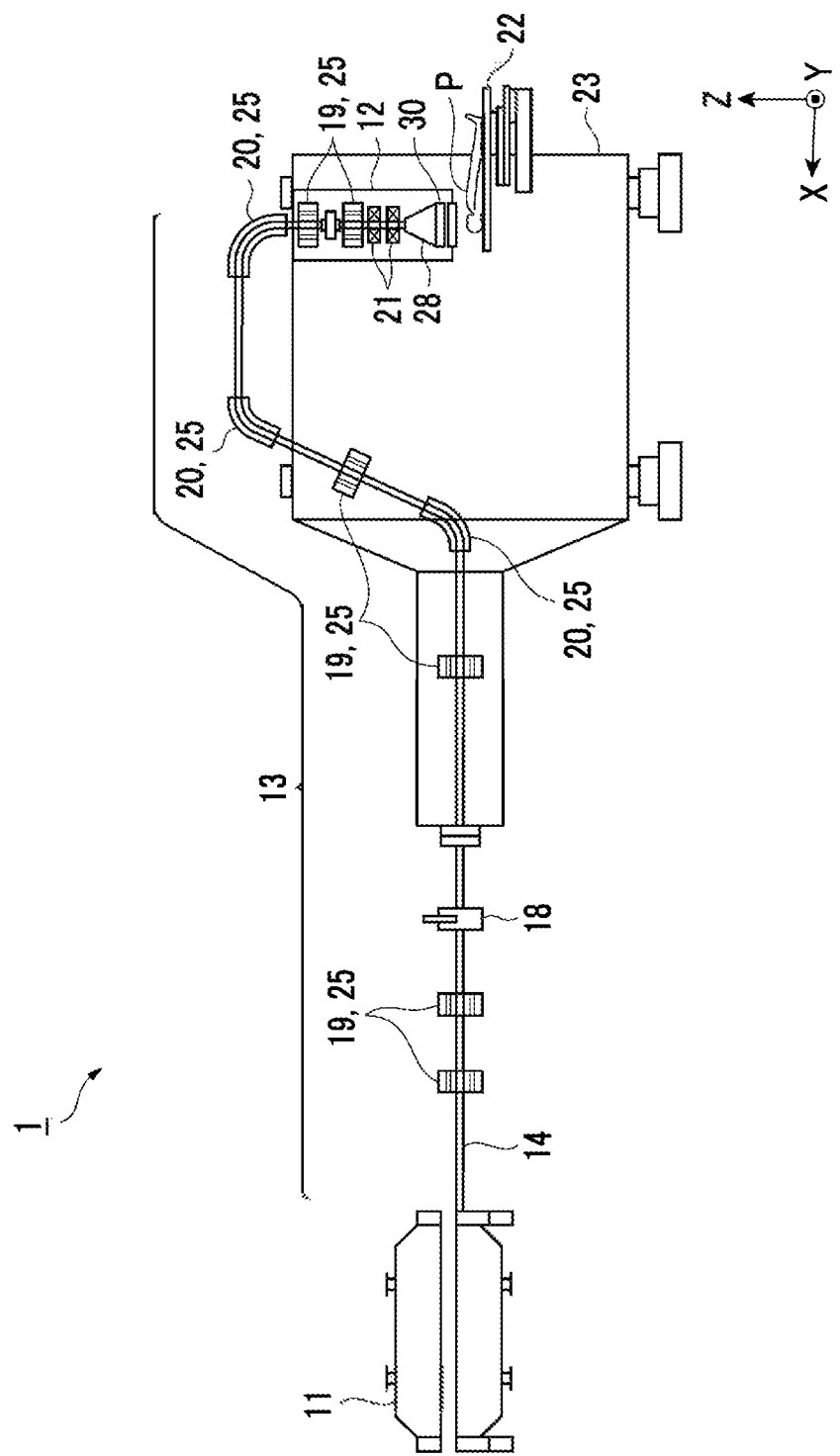
FIG. 1 is a schematic configuration diagram of a charged particle beam treatment apparatus according to an embodiment.

Incidentally, in a charged particle beam treatment apparatus which performs so-called scanning irradiation for irradiating an irradiation target body with a charged particle beam in accordance with a predetermined scanning pattern, it is conceivable to employ a multi-leaf collimator for the following purpose. A main purpose of the multi-leaf collimator is not to determine a shape of the irradiation field, but is to improve dose distribution in a peripheral edge of the irradiation field. That is, it is conceivable to employ the multi-leaf collimator in order to mainly reduce a dose rapidly rather than gradually in the peripheral edge of the irradiation field. However, if the multi-leaf collimator in the related art is applied to the charged particle beam treatment apparatus which performs the scanning irradiation, a space for moving a leaf included in a pair of leaf groups needs to be secured inside an irradiation nozzle. Consequently, there is a possibility that the irradiation nozzle may increase in size.

In a charged particle beam treatment apparatus for performing scanning irradiation, it is desirable to provide a charged particle beam treatment apparatus which can improve dose distribution of a charged particle beam in the peripheral edge of the irradiation field while preventing the irradiation nozzle from increasing in size.

According to the above-described charged particle beam treatment apparatus, the irradiation target body is irradiated with the charged particle beam used for scanning by the scanning unit through the multi-leaf collimator. Therefore, dose distribution of the charged particle beam is improved in the peripheral edge of the irradiation field. In at least a portion of the plurality of leaves of the multi-leaf collimator, the length in the direction along the second axis is shorter than the half of the length in the direction along the second axis of the maximum scanning range. Therefore, it is possible to reduce a space required for causing the leaves to move forward and rearward in the direction along the second axis. Thus, the multi-leaf collimator can be decreased in size. Accordingly, it is possible to improve the dose distribution of the charged particle beam while the irradiation nozzle is prevented from increasing in size.

According to an aspect of the embodiment, the charged particle beam treatment apparatus may further include a pair of blocking blocks that is disposed on both end sides of the leaf group in the direction along the first axis, whose length in the direction along the second axis is equal to or longer than the direction along the second axis of the maximum scanning range, and that blocks the charged particle beam.

Since the pair of blocking blocks is further provided as described above, the dose distribution can also be improved on both end sides of the leaf group.

According to another aspect of the embodiment, the leaf group may have a support unit for supporting the leaves. The leaves may be capable of oscillation around an axis along the first axis with respect to the support unit.

According to the above-described configuration, an angle of the leaf can be changed so as to correspond to an irradiation direction of the charged particle beam. Therefore, an advantageous effect of improving the dose distribution can be further achieved.

According to the embodiment of the present invention, there is provided a charged particle beam treatment apparatus which performs scanning irradiation. The charged particle beam treatment apparatus can improve dose distribution of a charged particle beam in a peripheral edge of an irradiation field while preventing an irradiation nozzle from increasing in size.

Figure 3:
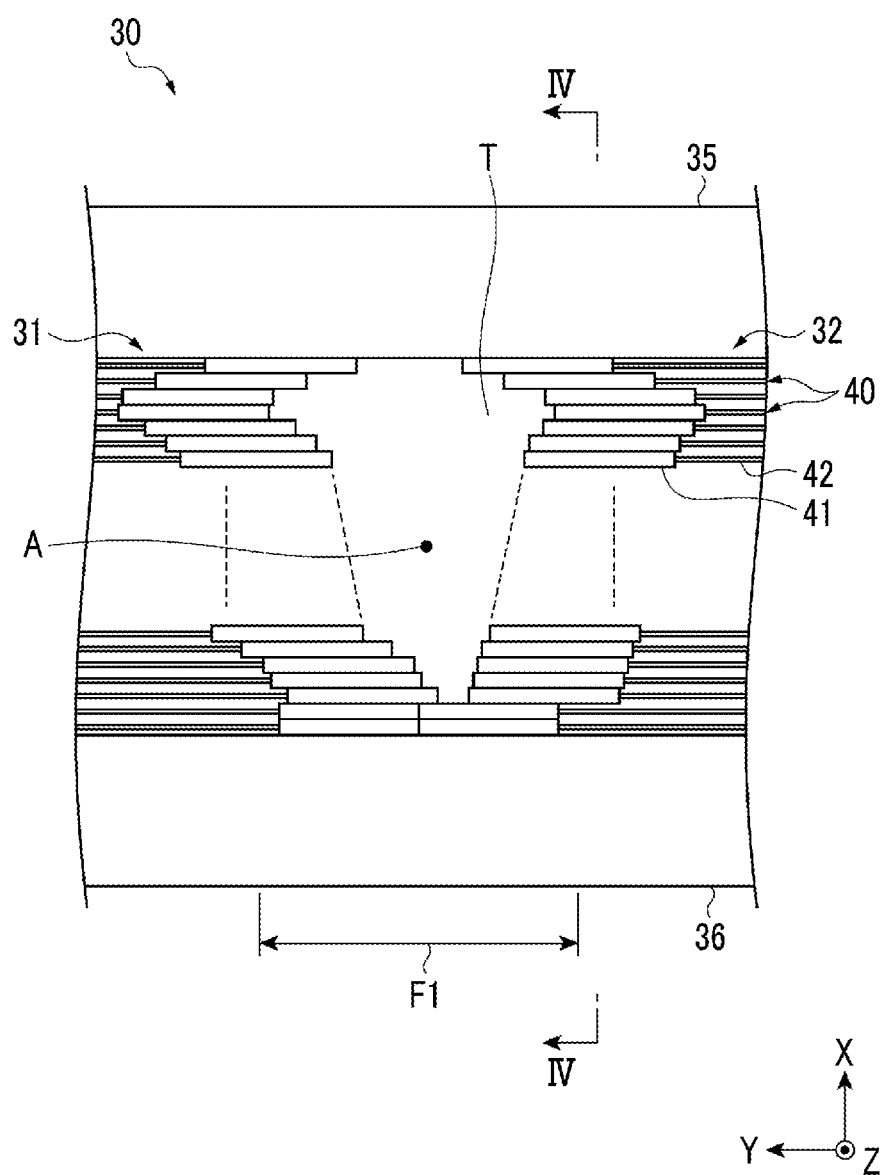
FIG. 3 is a plan view illustrating a main portion of the multi-leaf collimator.
Figure 4:
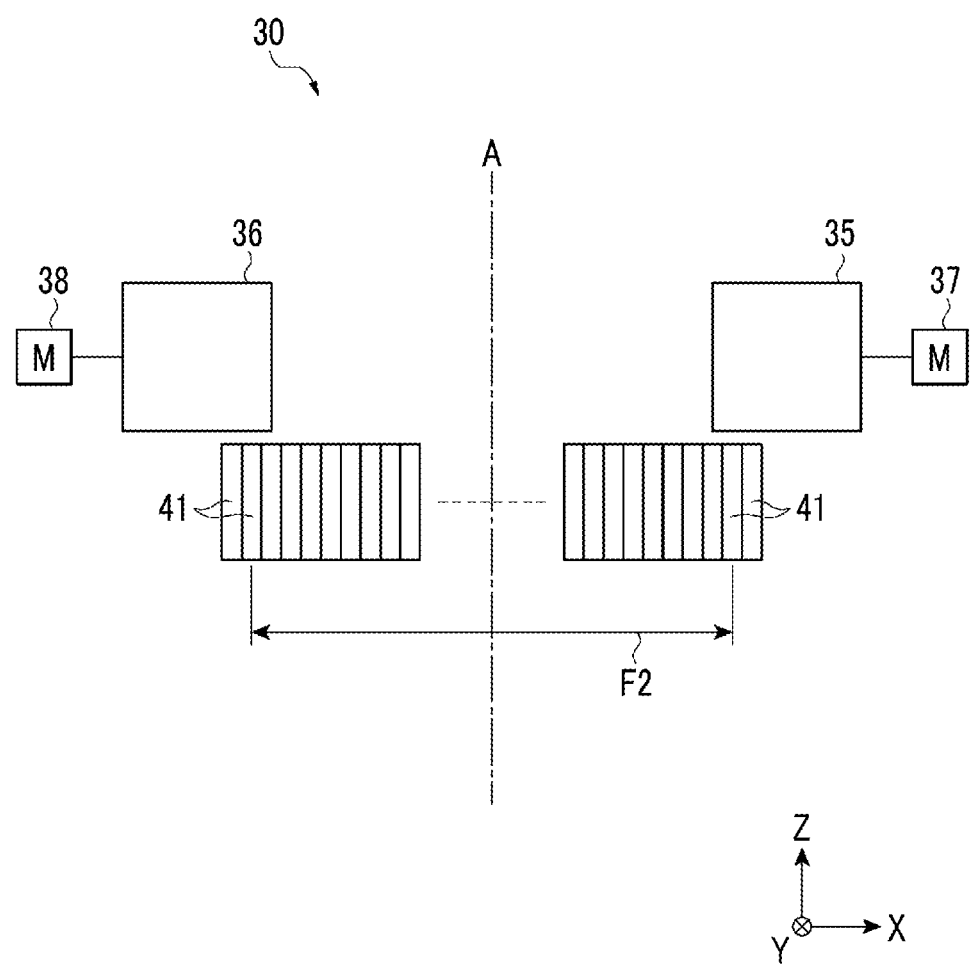
FIG. 4 is a view taken along line IV-IV in FIG. 3.

Hereinafter, the most preferable embodiment according to the present invention will be described in detail with reference to the accompanying drawings. In describing the drawings, the same reference numerals will be given to the same elements, and repeated description will be omitted. In order to facilitate the description, each drawing illustrates an XYZ-orthogonal coordinate system. In the following description, the XYZ-orthogonal coordinate system is used as follows. An extending direction of a Z-axis is set as an extending direction of a reference axis A in an irradiation direction of a charged particle beam. An extending direction of an X-axis (first axis) is set as a direction orthogonal to the z-axis. An extending direction of a Y-axis (second axis) is set as a direction orthogonal to the Z-axis and the X-axis. The reference axis A in the irradiation direction of the charged particle beam represents an axis through which a beam center of the charged particle beam passes in a case where the charged particle beam is used in irradiation without deflecting the charged particle beam in an irradiation nozzle 12 as illustrated in FIGS. 3 and 4.

As illustrated in FIG. 1, a charged particle beam treatment apparatus 1 is used for cancer treatment using radiotherapy, and includes an accelerator 11 that emits a charged particle beam by accelerating a charged particle generated in an ion source (not illustrated), an irradiation nozzle 12 (irradiation unit) that irradiates an irradiation target body with the charged particle beam, a beam transport line 13 (transport line) that transports the charged particle beam emitted from the accelerator 11 to the irradiation nozzle 12, a degrader (energy adjustment unit) 18 that is disposed in the beam transport line 13 so as to adjust an emitting range of the charged particle beam by reducing the energy of the charged particle beam, and a plurality of electromagnets 25 disposed in the beam transport line 13. In the present embodiment, a cyclotron is employed as the accelerator 11, but the accelerator 11 is not limited thereto. Other accelerators such as a cyclotron, a synchrotron, a synchrocyclotron, and a line accelerator may be used.

In the charged particle beam treatment apparatus 1, a tumor (irradiation target body) of a patient P on a treatment table 22 is irradiated with the charged particle beam emitted from the accelerator 11. The charged particle beam B is obtained by accelerating a charged particle at high speed, and includes a proton beam, or a heavy particle (heavy ion) ray, for example. The charged particle beam treatment apparatus 1 according to the present embodiment irradiates the irradiation target body with the charged particle beam by using a so-called scanning method. The irradiation target body is virtually divided (sliced) into a plurality of layers in a depth direction, and each layer (sliced plane) is irradiated with the charged particle beam for an irradiation range on the layer.

For example, an irradiation method using the scanning method includes spot-type scanning irradiation and raster-type scanning irradiation. In the spot-type scanning irradiation method, if one stop is completely irradiated within the irradiation range in one layer, irradiation using beam (charged particle beam) is stopped once. After irradiation preparation for the subsequent spot is ready, the subsequent spot is irradiated. In contrast, in the raster-type scanning irradiation method, the irradiation range in one layer is continuously irradiated with the beam without intermediately stopping the irradiation. In this way, in the raster-type scanning irradiation, the irradiation range in one layer is continuously irradiated with the beam. Accordingly, unlike the spot-type scanning irradiation, the irradiation range is not configured to include a plurality of spots. Hereinafter, an example will be described in which irradiation is performed using the raster-type scanning irradiation, but the embodiment of the present invention is not limited to this example. A configuration may be adopted in which the irradiation is performed using the spot-type scanning irradiation.

The irradiation nozzle 12 is attached to the inside of a rotary gantry 23 which is rotatable 360 degrees around the treatment table 22, and is movable to any rotational position by the rotary gantry 23. The irradiation nozzle 12 includes a converging electromagnet 19, a scanning electromagnet 21 (scanning unit), a duct 28, and a multi-leaf collimator 30. The scanning electromagnet 21 is disposed inside the irradiation nozzle 12. The scanning electromagnet 21 has an X-direction scanning electromagnet which scans a plane intersecting the irradiation direction (Z-direction) of the charged particle beam with the charged particle beam in the X-direction, and a Y-direction scanning electromagnet which scans a plane intersecting the irradiation direction (Z-direction) of the charged particle beam with the charged particle beam in the Y-direction intersecting the X-direction. The scanning electromagnet 21 can perform scanning in the X-direction and the Y-direction. The charged particle beam used for scanning by the scanning electromagnet 21 is deflected to the X-direction and/or the Y-direction. Accordingly, a diameter of the duct 28 on the downstream side from the scanning electromagnet 21 increases toward the downstream. The duct 28 is filled with gas for restraining divergence of the charged particle beam passing therethrough, or is internally brought into a vacuum state.

The multi-leaf collimator 30 shapes an irradiation field of the charged particle beam in accordance with a shape of the tumor (irradiation target body) of the patient P. The multi-leaf collimator 30 is disposed on the downstream side from the scanning electromagnet 21, in the vicinity of a lower end inside the duct 28. Details of the multi-leaf collimator 30 will be described later.

The beam transport line 13 has a vacuum duct 14 through which the charged particle beam passes. The vacuum duct 14 is internally maintained in a vacuum state, and restrains charged particles configuring the charged particle beam from being scattered due to air during transportation.

The degrader 18 on the beam transport line 13 reduces the energy of the charged particle beam passing therethrough, and adjusts an emitting range of the charged particle beam. A depth from a body surface of the patient P to the tumor serving as the irradiation target body varies depending on each patient. Accordingly, when the patient P is irradiated with the charged particle beam, it is necessary to adjust the emitting range which is an arrival depth of the charged particle beam. The degrader 18 adjusts the energy of the charged particle beam emitted from the accelerator 11 with predetermined energy, thereby adjusting the charged particle beam so as to properly reach the irradiation target body located at a predetermined depth inside the patient's body. The energy the charged particle beam is adjusted by the degrader 18 for each layer obtained by virtually slicing the irradiation target body. In a case where the accelerator 11 is a cyclotron, the energy of the charged particle beam is adjusted using the degrader 18. However, in a case where the accelerator 11 is a synchrotron, it is easy to adjust the energy of the charged particle beam. Accordingly, the degrader 18 can be omitted.

A plurality of electromagnets 25 are disposed in the beam transport line 13, and adjusts the charged particle beam so that the charged particle beam can be transported in the beam transport line 13 by using a magnetic field. The electromagnet 25 employs the converging electromagnet 19 for converging a beam diameter of the charged particle beam during transportation, and a deflection electromagnet 20 for deflecting the charged particle beam. In the following description, in some cases, the converging electromagnet 19 and the deflection electromagnet 20 are referred to as the electromagnet 25 without distinction therebetween. The plurality of the electromagnets 25 are disposed on the downstream side from the degrader 18 in at least the beam transport line 13. However, in order to converge the beam diameter of the charged particle beam before the energy is adjusted by the degrader 18, the plurality of the electromagnets 25 may be disposed on the upstream side from the degrader 18. The total number of the electromagnets 25 can be flexibly changed depending on the length of the beam transport line 13, and is set to approximately 10 to 40, for example.

An electromagnet power source which supplies a current for generating a magnetic field is connected to each of the electromagnets 25 (not illustrated). The current to be supplied to the electromagnet 25 is adjusted, thereby setting the strength of the magnetic field of the corresponding electromagnet 25.

An arrangement of the degrader 18 and the electromagnet 25 in the beam transport line 13 is not particularly limited.

Next, the multi-leaf collimator 30 disposed inside the irradiation nozzle 12 will be described with reference to FIGS. 2 to 4.

Figure 2:
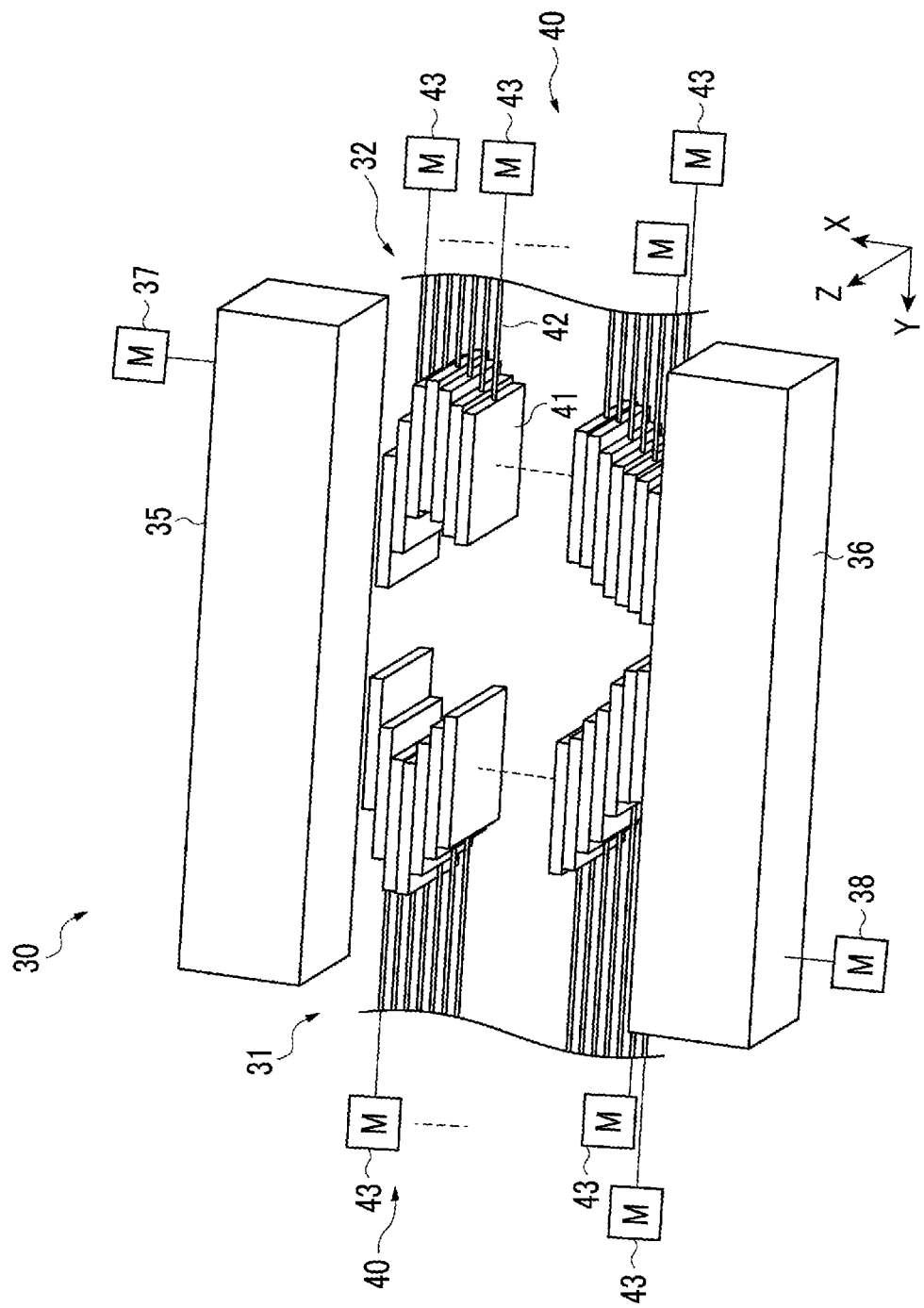
FIG. 2 is a schematic perspective view of a multi-leaf collimator.

FIG. 2 is a schematic perspective view illustrating the multi-leaf collimator 30, FIG. 3 is a plan view of the multi-leaf collimator 30 (viewed in the Z-direction), and FIG. 4 is a view taken along line IV-IV in FIG. 3.

The multi-leaf collimator 30 has a pair of leaf groups 31 and 32 facing each other in the Y-direction, and a pair of blocking blocks 35 and 36 disposed on both end sides of the pair of leaf groups 31 and 32 and facing each other in the X-direction.

As illustrated in FIG. 3, the pair of leaf groups 31 and 32 faces each other in the Y-direction across the reference axis A, in the XY-plane orthogonal to the reference axis A. Each of the pair of leaf groups 31 and 32 is configured to include a leaf member 40 including multiple leaves 41 which are independently movable forward and rearward in the Y-direction.

The leaf member 40 has the leaf 41, a support unit 42 for supporting the leaf 41, and a leaf drive unit 43 for moving the leaf 41. The leaf member 40 is disposed along the XY-plane so that the leaf 41 of the leaf member 40 included in the leaf group 31 and the leaf 41 of the leaf member 40 included in the leaf group 32 face each other.

The leaf 41 is a rectangular plate-shaped member which extends along the Y-direction. The leaf 41 is a member used for blocking the charged particle beam. Accordingly, the leaf 41 is manufactured using a material which can block the charged particle beam. As the material which can block the charged particle beam, brass, copper, tantalum, or molybdenum can be used. However, it is preferable to use brass which is excellent in blocking ability.

The width (length in the Z-direction) of the leaf 41 is set so that the charged particle beam can be blocked by the leaf 41. Therefore, in a case where the leaf 41 is made of brass which is excellent in blocking ability, the width of the leaf 41 can be narrowed. Accordingly, the multi-leaf collimator 30 can be decreased in size.

The length (length in the Y-direction) of the leaf 41 is set in accordance with the maximum scanning range of the charged particle beam. The maximum scanning range of the charged particle beam represents a range where the deflection of the charged particle beam can be controlled by the scanning electromagnet 21. The length of the leaf 41 can be shortened than ½ of the length in the Y-direction of the maximum scanning range of the charged particle beam. The lower limit of the length of the leaf 41 is preferably approximately 4 times the beam diameter of the charged particle beam emitted from the irradiation nozzle 12. The length of the leaf 41 is set to fall within the above-described range. In this manner, the multi-leaf collimator 30 can be decreased in size while the charged particle beam is reliably blocked.

The thickness (length in the X-direction) of the leaf 41 is not particularly limited. However, if the thickness of the leaf 41 is decreased, the irradiation field of the charged particle beam can be more finely shaped by the multi-leaf collimator 30.

A hard plating layer (hard coating layer) using electroless nickel plating may be formed on the surface of the leaf 41. The method for forming the hard plating layer is not limited to the electroless nickel plating, and various methods can be used. The hard plating layer may be partially or entirely formed on the surface of the leaf 41.

The support unit 42 for supporting the leaf 41 is a member which is attached to one side end portion in the longitudinal direction of the leaf 41 and which extends in the Y-direction. A material of the support unit 42 is not particularly limited. The support unit 42 may support the leaf 41 in a state where the leaf 41 is movable forward and rearward in the Y-direction. For example, as an example of such a configuration, a configuration may be adopted in which the support unit 42 itself is extendable. However, the support unit 42 itself may be formed of a rod-shaped member which does not extend.

The leaf drive unit 43 is driving means for moving the leaf 41 forward and rearward in the Y-direction. In a case where the support unit 42 of the leaf member 40 is configured to be extendable, an extending degree of the support unit 42 is changed by driving the leaf drive unit 43. In this manner, the leaf 41 can be controlled in moving forward and rearward in the Y-direct ion. In a case where the support unit 42 of the leaf member 40 does not extend, the support unit 42 is moved by driving the leaf drive unit 43. In this manner, the leaf 41 integrated with the support unit 42 can be controlled in moving forward and rearward in the Y-direction. A configuration may be adopted in which the leaf 41 is directly moved by the leaf drive unit 43. In this case, without providing the support unit 42, the leaf drive unit 43 and the leaf 41 are directly connected to each other.

When the pair of leaf groups 31 and 32 is viewed in the Y-direction, the pair of leaf groups 31 and 32 is disposed so that both ends in the X-direction within the maximum scanning range of the charged particle beam overlap the multiple leaves 41 included in the leaf groups 31 and 32. More specifically, as illustrated in FIG. 4, the multiple leaves 41 included in the leaf groups 31 and 32 are disposed so that the length in the X-direction of the leaf groups 31 and 32 is longer than the length of a maximum scanning range F2 of the charged particle beam when viewed in the Y-direction.

Each of the pair of blocking blocks 35 and 36 is a columnar member which extends along the Y-direction. The pair of blocking blocks 35 and 36 faces each other in the X-direction across the reference axis A, in the XY-plane orthogonal to the reference axis A and above (upper side along the Z-direction) the pair of leaf groups 31 and 32. That is, the blocking block 35 is disposed so as to connect end portions to each other on one side of the leaf groups 31 and 32, and the blocking block 36 is disposed so as to connect end portions to each other on the other side.

The blocking blocks 35 and 36 are members used for blocking the charged particle beam. Accordingly, the blocking blocks 35 and 36 are manufactured using a material which can block the charged particle beam. As the material which can block the charged particle beam, brass, copper, tantalum, or molybdenum can be used. However, it is preferable to use brass which is excellent in blocking ability.

The height (length in the Z-direction) of the blocking blocks 35 and 36 is set so that the charged particle beam can be blocked by the blocking blocks 35 and 36. Therefore, in a case where the blocking blocks 35 and 36 are made of tungsten or tantalum which is excellent in blocking ability, the height of the blocking blocks 35 and 36 can be lowered. Accordingly, the multi-leaf collimator 30 can be decreased in size.

The length (length in the Y-direction) of the blocking blocks 35 and 36 can be equal to or longer than the length in the Y-direction of the maximum scanning range of the charged particle beam. As illustrated in FIG. 3, the blocking blocks 35 and 36 are disposed so as to entirely include a maximum scanning range F1 of the charged particle beam in the Y-direction.

The width (length in the X-direction) of the blocking blocks 35 and 36 is not particularly limited. However, it is preferable that the width is approximately 4 times the beam diameter of the charged particle beam emitted from the irradiation nozzle 12. The width of the blocking blocks 35 and 36 is set to fall within the above-described range. In this manner, the multi-leaf collimator 30 can be decreased in size while the charged particle beam is reliably blocked.

The blocking blocks 35 and 36 are respectively connected to the block drive units 37 and 38. The blocking blocks 35 and 36 are movable forward and rearward in the X-direction of the blocking blocks 35 and 36 by driving the block drive units 37 and 38.

In the above-described multi-leaf collimator 30, the multiple leaves 41 included in the pair of leaf groups 31 and 32 are moved forward and rearward in the Y-direction, and the pair of blocking blocks 35 and 36 is moved forward and rearward in the X-direction. In this manner, an opening T (refer to FIG. 3) can be formed at the center. A shape of the opening T is aligned with a shape of the irradiation target body. In this manner, an irradiation field of the charged particle beam can be regulated. The shape of the opening T is set in accordance with a sliced plane (layer) in which the irradiation target body is irradiated with the charged particle beam.

Here, in the charged particle beam treatment apparatus 1 according to the present embodiment, the charged particle beam emitted from the accelerator 11 and transported by the beam transport line 13 is deflected in a predetermined direction by the scanning electromagnet 21. The opening T formed by the multi-leaf collimator 30 further defines the irradiation field, and the patient P is irradiated with the charged particle beam.

In the related art, the multi-leaf collimator is generally applied to the charged particle beam treatment apparatus using a broad beam method (widened irradiation method). The charged particle beam treatment apparatus using the broad beam method employs the multi-leaf collimator for the charged particle beam whose beam diameter is larger than the irradiation target body. In this manner, the patient P is irradiated with the charged particle beam by cutting out the charged particle beam having the irradiation field corresponding to the shape of the irradiation target body.

On the other hand, according to the charged particle beam treatment apparatus which performs the scanning irradiation, the irradiation target body is irradiated with the charged particle beam, based on the scanning pattern corresponding to the irradiation target body. Thus, it is considered that a device for shaping the irradiation field such as the multi-leaf collimator is unnecessary. However, it is found that the charged particle beam treatment apparatus which performs the scanning irradiation also has room for improvement in the penumbra (lateral penumbra) of the charged particle beam emitted from the irradiation nozzle. That is, it is desirable that the dose distribution of the beam emitted from the irradiation nozzle is uniform. However, a possibility is conceivable that the dose distribution may decrease in the beam edge and the dose of the charged particle beam may gradually decrease in the end portion of the irradiation field.

Therefore, the charged particle beam treatment apparatus 1 according to the present embodiment employs the multi-leaf collimator 30 while performing the scanning irradiation of the charged particle beam. In this manner, the charged particle beam is blocked by the leaf 41. Accordingly, it is possible to improve the dose distribution of the charged particle beam, especially in the peripheral edge of the irradiation field, thereby enabling the dose to be rapidly changed in the peripheral edge.

In the multi-leaf collimator 30 in the charged particle beam treatment apparatus 1 according to the present embodiment, the length of the leaf 41 is shorter than a half of the length in the Y-direction of the scanning range of the charged particle beam. In this manner, a size of the space occupied by the multi-leaf collimator 30 can be decreased in size, and the charged particle beam treatment apparatus 1 can also be decreased in size.

In the charged particle beam treatment apparatus using the broad beam method (widened irradiation method), the multi-leaf collimator is used so that the charged particle beam having the beam diameter larger than that of the irradiation target body is shaped into the irradiation field corresponding to the irradiation target body. Accordingly, it is necessary to prepare the leaf which can block all charged particle beams, and thus, the leaf needs to be lengthened. In this case, a space for allowing the movement of the leaf needs to be disposed outside the pair of leaf groups. Accordingly, the space occupied by the multi-leaf collimator increases in size. Therefore, the irradiation nozzle itself which accommodates the multi-leaf collimator increases in size.

In contrast, in the charged particle beam treatment apparatus 1 which performs the scanning irradiation according to the present embodiment, the beam diameter of the charged particle beam is extremely smaller than that in the broad beam method, and is used in controlling the dose distribution of the charged particle beam in the peripheral edge of the irradiation target body. Accordingly, the leaf can be sufficiently decreased in size. Therefore, since the space for allowing the movement of the leaf can also be decreased in size, the space occupied by the multi-leaf collimator 30 can be decreased in size, and the irradiation nozzle can also be decreased in size.

If the leaf 41 in the multi-leaf collimator 30 decreases in size, the movement of the leaf 41 is facilitated. Therefore, since the leaf 41 can be more quickly moved, the opening T can be more quickly controlled in the multi-leaf collimator 30.

Furthermore, if the support unit 42 of the leaf member 40 is configured to be extendable, the movement amount of the support unit 42 moved by the movement of the leaf member 40 can be reduced. Therefore, it is unnecessary to secure a space for the support unit 42 moved by the movement of the leaf 41, and the space occupied by the multi-leaf collimator 30 can be further decreased in size.

In order to achieve the improved advantageous effect of the dose distribution of the charged particle beam by using the leaf 41 of the leaf member 40, it is preferable to adopt a configuration in which the leaf 41 is capable of oscillation around the X-direction. This point will be described with reference to FIG. 5.

Figure 5:
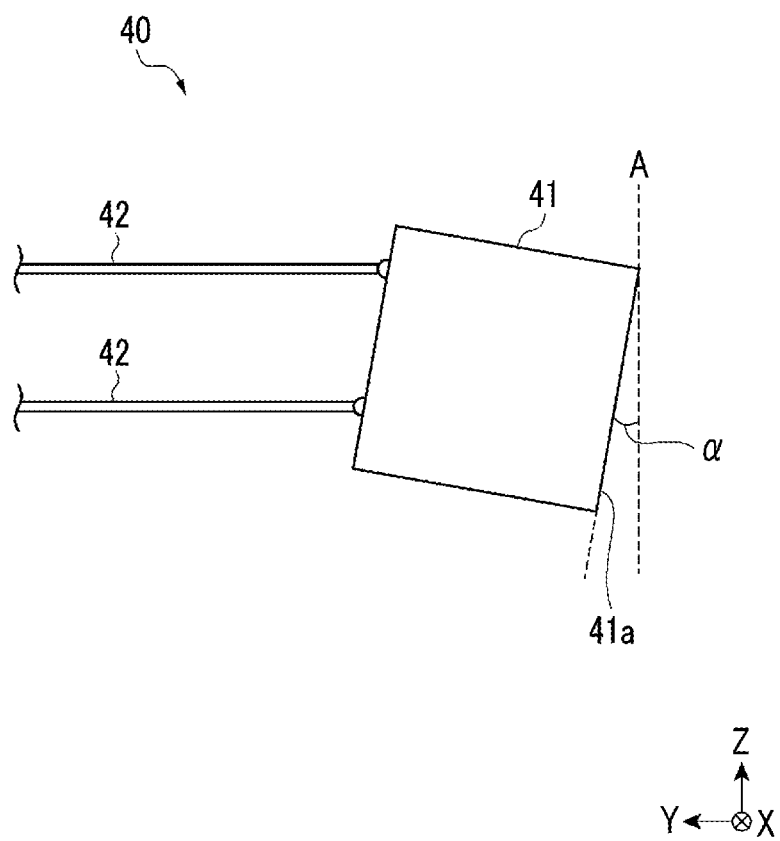
FIG. 5 is a view illustrating a modification example of a leaf member.

FIG. 5 illustrates a configuration in which the leaf 41 of the leaf member 40 pivots around the X-direction along a YZ-plane and an end surface 41a is inclined by an angle α with respect to the extending direction (Z-direction) of the reference axis A. The end surface 41a is located on a side facing the leaf group. The angle α is set in accordance with the irradiation direction of the charged particle beam.

In the charged particle beam treatment apparatus 1 which performs the scanning irradiation, the charged particle beam is deflected for irradiation by the scanning electromagnet 21. Accordingly, as the irradiation position of the charged particle beam moves away from the reference axis A, the irradiation is performed in a state where the charged particle beam is inclined with respect to the reference axis A. In this way, if the irradiation is performed in the state where the charged particle beam is inclined with respect to the reference axis A, there is a possibility that the dose of the charged particle beam may gradually decrease in the peripheral edge of the irradiation field. In contrast, the leaf 41 is configured to be capable of oscillation around the axis extending in the X-direction with respect to the support unit 42, thereby adopting a configuration in which the end surface of the leaf 41 is inclined in accordance with the inclination of the charged particle beam. In this manner, the charged particle beam can be restrained from being scattered in the end portion of the leaf 41, and the dose distribution of the charged particle beam can be further improved.

A method of adopting the configuration in which the leaf 41 is capable of oscillation around the axis extending in the X-direction with respect to the support unit 42 is not particularly limited. For example, in the example of FIG. 5, two support units 42 are attached to the leaf 41, and each support unit 42 is attached to the leaf 41 so as to be pivotable around the X-direction. According to this configuration, two holding members are caused to have mutually different movement amounts in the Y-direction. In this manner, the leaf 41 is capable of oscillation around the axis extending in the X-direction.

Figure 6A:
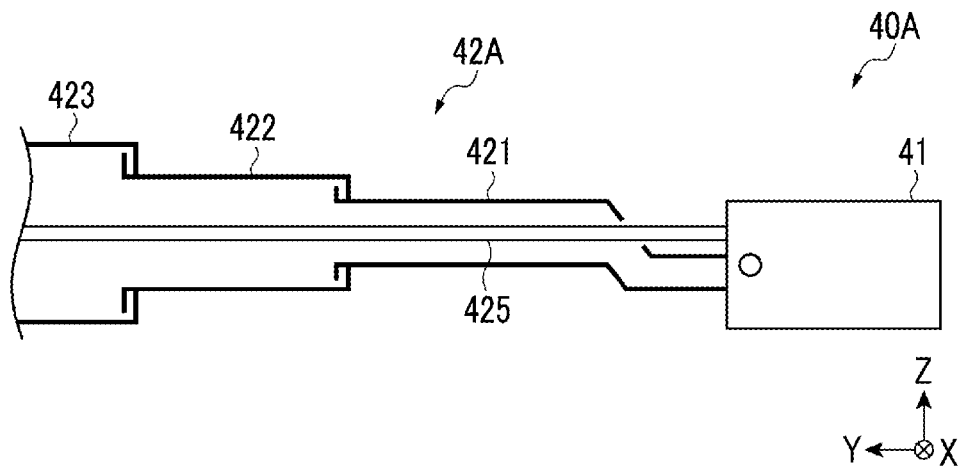
FIGS. 6A to 6C are views illustrating each modification example of the leaf member.
Figure 6B:
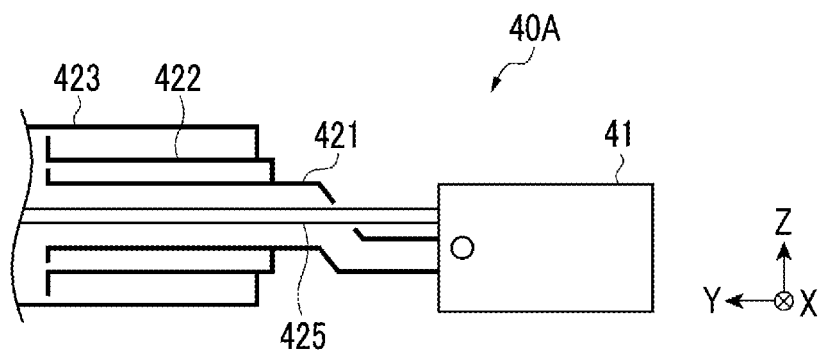
Figure 6C:
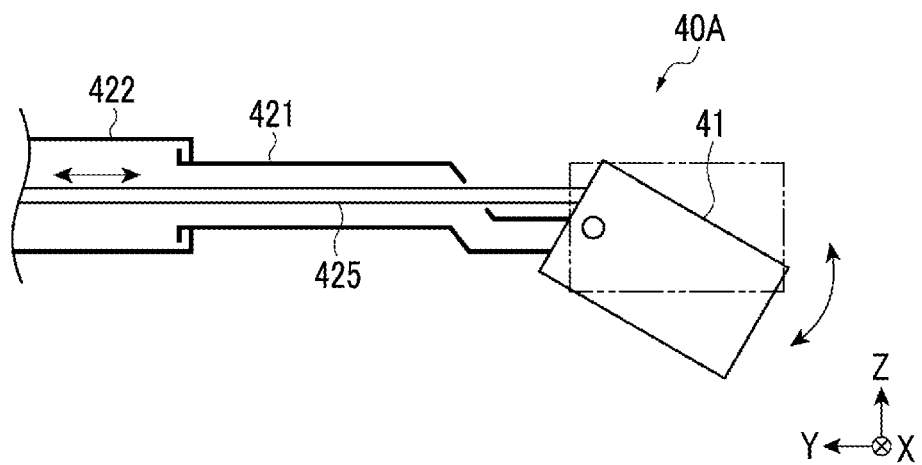

Furthermore, FIG. 6A to 6C illustrate each configuration in which the support unit is extendable, and illustrate each example of a leaf member 40A whose leaf is capable of oscillation with respect to the support unit. FIGS. 6A to 6C are views for describing a configuration of the leaf member 40A, and a procedure in which a support unit 42A extends and the leaf 41 oscillates.

In the leaf member 40A illustrated in FIG. 6A, the support unit 42A is configured to include a plurality of cylindrical members 421, 422, and 423 having a rod shape. The cylindrical members 421, 422, 423 are connected to each other so as to be slidable in this order along the Y-direction. The outer diameters become larger in the order of the cylindrical member 421 located on the distal side (leaf 41 side), the cylindrical member 422 connected to the cylindrical member 421, and the cylindrical member 423 connected to the cylindrical member 422. The cylindrical member 421 can be accommodated inside the cylindrical member 422, and the cylindrical member 422 can be accommodated inside the cylindrical member 423. The cylindrical member 421 is attached so as to be pivotable around the axis extending in the X-direction with respect to the leaf 41. Apart from the cylindrical member 421, for example, a rod-shaped member 425 formed of a wire extending in the Y-direction is attached so as to be pivotable around the axis extending in the X-direction with respect to the leaf 41.

In a case of the above-described leaf member 40A, a relative position of the cylindrical members 421, 422, and 423 is changed. In this manner, the leaf 41 is movable forward and rearward in the Y-direction. For example, as illustrated in FIG. 6A, the cylindrical members 421, 422, and 423 are brought into a state where all of these extend in this order in the Y-direction, thereby causing the leaf 41 to move in the Y-direction. As illustrated in FIG. 6B, the cylindrical members 421 and 422 are brought into a state where both of these are accommodated inside the cylindrical member 423, that is, a state where the cylindrical members 421, 422 and 423 overlap each other, thereby causing the leaf 41 to move in the Y-direction. The relative position in the Y-direction of the rod-shaped member 425 is changed with respect to the cylindrical members 421, 422, and 423. In this manner, as illustrated in FIG. 6C, the leaf 41 is capable of oscillation around the axis extending in the X-direction with respect to the support unit 42A.

As described above, the configuration of the leaf member 40A, particularly, the configuration for controlling the forward and rearward movement of the leaf 41 in the Y-direction and the oscillation around the axis extending in the X-direction can be changed in various ways.

The embodiment of the present invention is not limited to the above-described embodiment. For example, as long as the multi-leaf collimator 30 is located inside the irradiation nozzle 12 on the downstream from the scanning electromagnet 21, the attachment position is not limited.

The structure of the multi-leaf collimator 30 can be appropriately changed. For example, a configuration has been described in which each of the pair of blocking blocks 35 and 36 includes one block. However, each of the blocking blocks 35 and 36 may be configured to include a plurality of blocks. The shape of the leaf 41 or the structure for moving the leaf 41 forward and rearward in the Y-direction can be appropriately changed. The mechanism and the arrangement of the leaf drive unit for moving the leaf forward and rearward can be appropriately changed.

It should be understood that the invention is not limited to the above-described embodiment, but may be modified into various forms on the basis of the spirit of the invention. Additionally, the modifications are included in the scope of the invention.

What is claimed is:

1. A charged particle beam treatment apparatus which irradiates an irradiation target body with a charged particle beam, comprising:
   an accelerator configured to generate and emit the charged particle beam;
   an irradiation nozzle configured to irradiate the irradiation target body with the charged particle beam; and
   a transport line that connects the accelerator and the irradiation nozzle to each other so as to transport the charged particle beam, wherein an axis orthogonal to a reference axis when the irradiation target body is irradiated with the charged particle beam is set to as a first axis, and an axis orthogonal to the reference axis and the first axis is set to as a second axis, wherein the irradiation nozzle has a scanning unit which can scan the irradiation target body with the charged particle beam within a predetermined maximum scanning range in a direction along the first axis and a direction along the second axis, and a multi-leaf collimator which is disposed on a downstream side from the scanning unit, and which regulates a shape of an irradiation field when the irradiation target body is irradiated with the charged particle beam, wherein the multi-leaf collimator has a pair of leaf groups disposed to face each other across the reference axis, wherein the leaf group has a plurality of leaves which are arrayed in the direction along the first axis, which are independently movable forward and rearward in the direction along the second axis, and which blocks the charged particle beam, and a leaf drive unit which causes the leaves to move forward and rearward in the direction along the second axis, wherein in at least a portion of the plurality of leaves, a length of respective ones of the plurality of leaves in the direction along the second axis is shorter than a half of a length along the second axis of the maximum scanning range, and wherein each of the plurality of leaves is independently configured to oscillate around a third axis extending in a same direction as the first axis.

2. The charged particle beam treatment apparatus according to claim 1, further comprising:
a pair of blocking blocks that is disposed on both end sides of the leaf group in the direction along the first axis, whose length in the direction along the second axis is equal to or longer than the direction along the second axis of the maximum scanning range, and that blocks the charged particle beam.

3. The charged particle beam treatment apparatus according to claim 1,
wherein the leaf group has a support unit for supporting the leaves, and
wherein the leaves are independently configured to oscillate around an axis along the first axis with respect to the support unit.

* * * * *